United States Patent [19]

Cieslak

[11] Patent Number: 4,685,442
[45] Date of Patent: Aug. 11, 1987

[54] PORTABLE HEATER FOR WEARING APPAREL

[76] Inventor: Leonard Cieslak, 15 Creek Rd., McKees Rocks, Pa. 15136

[21] Appl. No.: 5,268

[22] Filed: Jan. 20, 1987

[51] Int. Cl.$^4$ .............................................. A61F 7/08
[52] U.S. Cl. ..................................... 126/204; 126/206; 36/2.6; 128/403; 128/383; 165/46
[58] Field of Search ............... 126/206, 208, 204, 263; 128/383, 382, 400, 402, 403; 36/2.6; 165/46

[56] References Cited

U.S. PATENT DOCUMENTS

| | | | |
|---|---|---|---|
| 912,527 | 2/1909 | Batter. | |
| 2,648,325 | 6/1952 | Siple | 126/204 |
| 3,000,616 | 10/1958 | Spangler | 257/12 |
| 3,712,288 | 1/1973 | Weiss | 126/206 |
| 4,180,922 | 1/1980 | Cieslak et al. | 36/2.6 |
| 4,281,418 | 8/1981 | Cieslak et al. | 2/160 |
| 4,286,571 | 9/1981 | Hung | 126/206 |
| 4,334,519 | 6/1982 | Cieslak et al. | 126/204 |
| 4,441,483 | 4/1984 | Cieslak et al. | 126/206 |

*Primary Examiner*—Randall L. Green
*Attorney, Agent, or Firm*—Carothers & Carothers

[57] ABSTRACT

A portable heater for generating and circulating heat in wearing apparel and consisting of a closed container for containing a liquid heat transfer medium therein and a second container which is received in the closed container and is adapted to receive a heat evolving means therein such as a combustible fuel stick of the type utilized in conventional hand warmers, the heat evolving means being received through an opening to the exterior of the improved heater assembly. A portion of the exterior walls of the second container are exposed in heat exchange relationship to the interior of the closed container for efficient heat transfer through the walls of the second container to a liquid heat transfer medium contained within the closed container. A flexible liquid conduit has both ends thereof connected to the heater assembly for circulation of the hot liquid medium from the closed container through the conduit to an article of wearing apparel, and a portion of the closed container comprises a positive displacement pump that is cooperable with the conduit and is operable by hand manipulation to circulate the heated liquid medium from the closed container through the conduit and the article of wearing apparel on demand.

20 Claims, 4 Drawing Figures

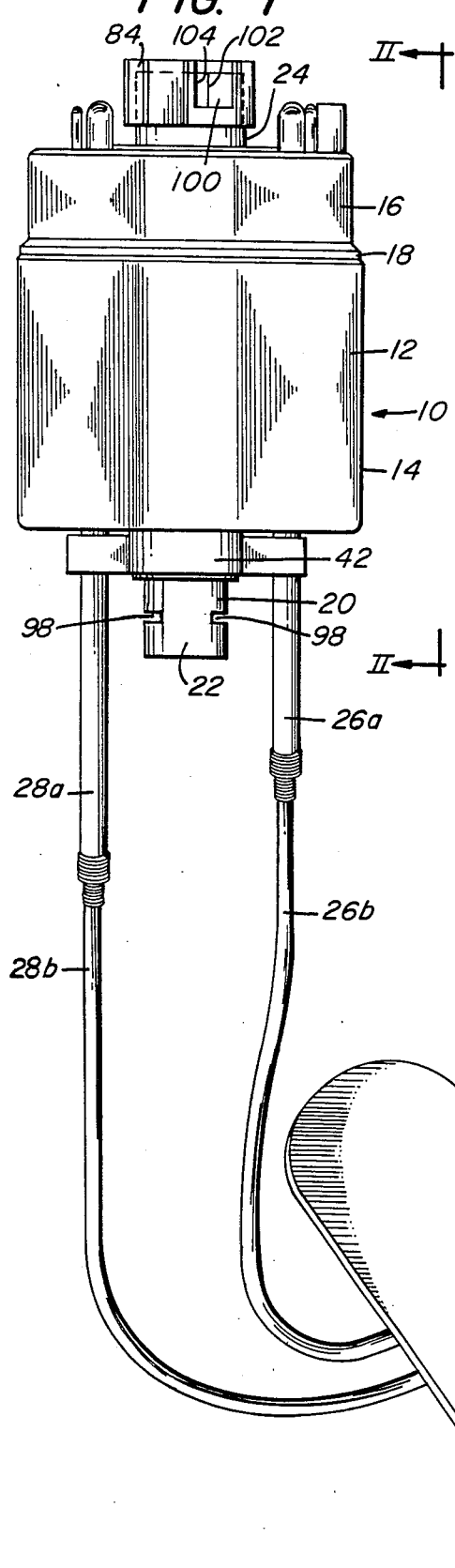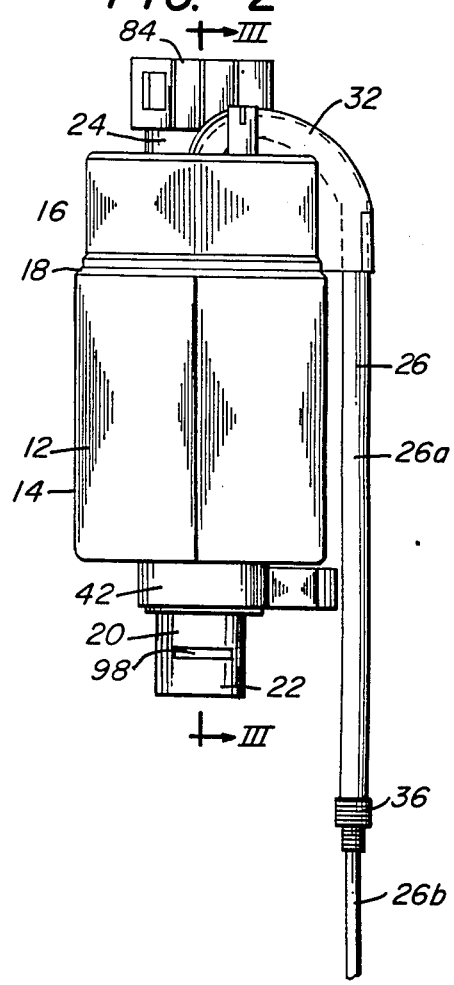

PORTABLE HEATER FOR WEARING APPAREL

BACKGROUND OF THE INVENTION

The present invention relates to portable heaters and more particularly to compact heaters or warmers to be carried on the person for circulating heat in wearing apparel such as gloves or boots. Many prior heating systems for this purpose are known in the art. Most notably, I am an inventor in each of the following four prior patents, all of which disclose such portable heating systems: U.S. Pat. Nos. 4,180,922; 4,281,418; 4,334,519; and 4,441,483. The entire disclosure of each of the above cited patents is hereby incorporated herein and made a part hereof by reference.

Other prior art patents known to me which are pertinent to heaters or warming apparatus for wearing apparel include the following. U.S. Pat. No. 2,648,325 discloses a jacket equipped to impart heat to the body of a wearer by including self-contained means for generating heat which comprises a warm liquid circulating system means that is actuated by breathing of the jacket wearer to cause circulation of the liquid through a network of conduits. The apparatus of this patent includes a heater such as a catalytic or chemical heater. The patent also discloses bulbs which form a part of the liquid circulation system and which may be alternately compressed and released to enhance flow of liquid in the system.

U.S. Pat. No. 3,000,616 discloses an air charged body warmer in which periodic collapse of one or more bladder-like members cooperates with a system of check valves to produce circulation through a closed conduit system in conjunction with normal working or running activities.

U.S. Pat. No. 912,527 discloses a portable foot and body warmer wherein a lamp chamber contains a heater element which heats fluid that flows through a combined pump and heat exchange unit.

U.S. Pat. No. 3,712,288 discloses a hand warmer glove with a bladder pump which is separate from the warming element and which pump is utilized to extract or draw heated air from around the heater element for delivery thereof throughout the glove to warm the hand and fingers.

There are, of course, a great many additional prior art references which disclose conventional hand warmers or other portable furnace devices, as well as such devices in combination with various garments such as vests, body suits, boots and shoes, mittens, bicycle handgrips, body wraps, and the like.

BRIEF SUMMARY OF THE INVENTION

The portable heater of the present invention for heating wearing apparel or the like generally comprises a compact, closed container for containing a liquid heat transfer medium therein, which container is capable of being readily carried on ones person. A second and smaller container is received within this first-mentioned container and is adapted to receive a heating element therein, such as a solid fuel agglomerate or a chemical heating unit. The heating element is inserted into the second container through an opening which is accessible from the exterior of the entire portable heater assembly. At least a portion of the exterior wall surfaces of the second container, and preferably a major part thereof, are exposed in heat exchange relationship to the interior of the closed container to provide heat exchange through the walls of the second container to the heat transfer medium contained within in the closed container.

A flexible liquid conduit has the opposite ends thereof connected to the heater unit for circulation of heated liquid heat transfer medium from the liquid container through the conduit and to an article of wearing apparel, and thence back to the heating unit. To the extent the invention has been summarized thus far, it is similar in many respects to certain of those portable heater devices which are the subject of the above cited patents in which I am an inventor. The present invention, however, provides a novel and improved positive displacement pump that is operable by hand manipulation to circulate heated liquid from the liquid reservoir or container through the conduit system and the connected wearing apparel on demand. One aspect of the improved positive displacement pump arises in having a portion of the liquid container formed as a resiliently deformable sealed envelope or reservoir that is cooperable with the conduit system and other elements to provide the improved pumping action, and another portion of the heater unit functions as an ambient pressure fluid receiving tank which receives heat transfer medium circulating from wearing apparel back to the heater, and is cooperable with the improved pump to gravitationally resupply the combined fluid heating chamber, reservoir and pump chamber on demand.

A further aspect of the invention includes a removable cap which selectively closes an access opening from the exterior of the heater assembly into the second or heating element receiving container. The removable cap also provides a vent which is cooperable with other vent means provided in the heating element receiving container to provide a draft for slow combustion of a combustible fuel element or to provide ventilation for gases evolved in use of a chemical heating element. The cap preferably is formed from known thermal insulating plastic such as that used for cookware handles. One such plastic material includes glass particles dispersed therein and forming approximately 35% of the plastic material composition.

In one embodiment of the invention, the inner or heating element receiving container may take form of an elongated tube which passes through the liquid container such that exterior surface portions of the sidewalls of the tubular element are exposed to the interior of the liquid container for heat exchange through the sidewalls of the tube from the heat evolving fuel therein to the liquid heat transfer medium within the liquid container.

Other features of the invention includes overall structural simplification over known prior heaters of this general type, and enhanced ease of operation and reliability owing to both simplified structure and the novel design features above mentioned. The invention thus provides a portable heater which is very inexpensive and easy to manufacture owing to reduced assembly effort and material costs, and yet which provides improved efficiency and ease of operation in achieving the desired result in use.

It is therefore one general object of this invention to provide a novel and improved portable heater apparatus.

A more specific object of the invention is to provide a portable heater apparatus of simplified structure and assembly.

Another object of the invention is to provide a portable heater apparatus with combined fuel receiving chamber, heat exchange surfaces, heat transfer medium reservoir, pump chamber, and return fluid chamber in a single compact assembly.

BRIEF DESCRIPTION OF THE DRAWINGS

These and other objects and further advantages of the invention will be more fully understood upon consideration of the following detailed description and the accompanying drawings, in which:

FIG. 1 is a frontal elevation of a portable heater apparatus according to one presently preferred embodiment of the invention;

FIG. 2 is a side elevation taken generally from line II—II of FIG. 1;

DETAILED DESCRIPTION OF THE PREFERRED EMBODIMENT

Figure 3:
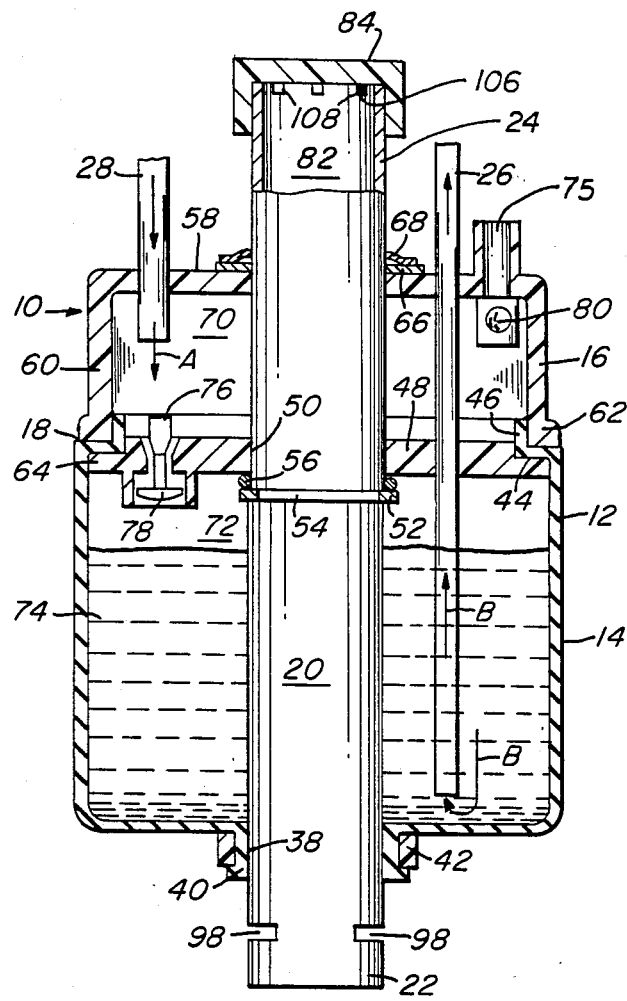
FIG. 3 is a transverse section taken on line III—III of FIG. 2.

There is generally indicated at 10 in FIGS. 1 through 3 a portable heater apparatus according to one presently preferred embodiment of the instant invention and comprising a body assembly 12 that includes a lower resiliently flexible portion 14 and an upper rigid portion 16 which are joined at an interface 18 to form a sealed body unit.

An elongated, generally tubular open ended heating element container 20 extends through body portions 14 and 16, and has respective longitudinal end portions 22 and 24 thereof extending outwardly of the respective body portions 14 and 16.

As best shown in FIGS. 1 and 2, a pair of fluid flow conduits 26 and 28 are connected to body assembly 12, penetrating the rigid body portion 16 adjacent an uppermost extent thereof and extending therefrom to an article of wearing apparel such as an innersole member 30 which may be placed in a boot or other foot wear (not shown). The innersole member 30 incorporates therein a network of liquid flow channels which are connected to the conduits 26 and 28 for purposes of allowing the circulation of heated fluid from heater 10 via conduit 26 to warm innersole member 30, the fluid thence returning via conduit 28 to heater 10.

As shown in FIG. 2, rigid body member 16 may be a molded plastic member and may include upstanding tube guides 32 to guide tubes 26 and 28 generally downwardly along the backside of the heater 10 so that tubes 26 and 28 may extend therefrom to the innersole 30. This would be a useful configuration when, for example, the heater 10 is being carried by a user at his belt line by means of suitable spring clips or the like (not shown) affixed to the heater 10 by suitable fastening thereof to one or more tabs 34 which are formed integrally with guides 32 and the rest of rigid body member 16. The conduit 26 need not be a continuius run of tubing, for as shown in FIG. 2 it may be comprised of relatively larger and smaller diameter tubing runs 26a and 26b secured together in any suitable manner such as by a wire nut type fastener 36 which takes the form of a helically wound spring having a relatively larger diameter extent and a relatively smaller diameter extent as shown in FIG. 2.

As best shown in FIG. 3, the body assembly 12 provides a return fluid receiving chamber, a heating chamber, a pumping chamber, a fuel containment chamber for heat evolution, and a fluid inlet means. Specifically, resilient body portion 14 is formed from rubber or the like to encompass an intermediate longitudinal portion of tube 20. Tube 20 thus extends through a lower opening or aperture 38 extending through a collar portion 40 of member 14. A fluid tight sealed interface between tube 20 and collar 40 is formed by application of a circumferential clamp 42 which may be any suitable circumferential clamp structure such as a conventional hose clamp, or a plastic cable tie, for example.

The uppermost end portion of resilient member 14 is formed, at interface 18, to provide a radially inwardly projecting shoulder 44 and contiguous upwardly projecting flange portion 46. A rigid, inner wall member 48 resides within resilient member 14 adjacent the lower side of shoulder 44 and in sealed engagement therewith. Wall member 48 includes an aperture 50 which receives a longitudinally intermediate portion of tube 20 therein. A fluid tight seal between aperture 50 and tube 20 is provided by means of a snap ring 52 that is received within a circumferential groove 54 formed on the outer surface of tube 20 downwardly adjacent wall member 48, and an O-ring seal member 56 encompassing tube 20 intermediate snap ring 52 and wall member 48. O-ring 56 is compressed in a manner to be described hereinbelow to provide the desired sealing effect.

Rigid body portion 16 comprises, as shown in FIG. 3, an inverted cup like form having a transverse base portion 58 and a circumferential skirt portion 60 having a lowermost end 62 which engages upper and outer portions of shoulder 44 and flange 46 such that these are captively and sealingly retained between the circumferentially extending lower end portion 62 of rigid member 16, and the radially outermost extending portion 64 of wall member 48.

Adjacent the upper side of base portion 58, a suitable sealing washer 66 and a spring toothed washer 68 encompass tube 20 and are forced downwardly thereon to tightly and sealingly clamp the rigid body member 16 and wall member 48 between the toothed washer 68 and the snap ring 52. Washer 68 has a plurality of circumferentially distributed, radially projecting teeth which frictionally engage tube 20 to firmly grip same and maintain the washer 68 in clamping engagement thereon. This clamping action deforms O-ring seal 56 into fluid sealing engagement about tube 20 and adjacent portions of wall member 48. In addition, the clamping action provides compressive sealed engagement of shoulder 44 and flange 46 between the portions 62 and 64 of rigid body member 16 and wall member 48, respectively. In this manner, separate fluid chambers 70 and 72 are provided on opposite sides of wall member 48. Chamber 70 is a fluid return chamber which receives liquid from conduit 28 as indicated by arrow A while chamber 72 is a combined liquid medium heating and pumping chamber which is operable to permit heating of a liquid heat transfer medium 74 such as water or a water and antifreeze mixture, and to provide for pumping thereof via conduit 26 to inner sole 30 as indicated by arrow B. To effect this purpose, it is noted that conduit 26 extends through suitable aligned apertures in base portion 58 and wall member 48 nearly all the way to the bottom of chamber 72 as shown. Conduit 28, on the other hand, merely penetrates base portion 58 so that an open end thereof resides within chamber 70.

Other structural features of assembly 10 include an inlet port 75 which facilitates loading of fluid medium into the apparatus 10, the fluid being injected into port 75 and flowing therefrom into chamber 70 and thence via a one-way flow check valve 76 to fill the chamber 72. As shown, check valve 76 comprises a float valve element having a seat portion 78 which is operable by fluid flow impetus or gravity to preclude both backflow of fluid and airflow from chamber 72 to chamber 70 for purposes to be described hereinbelow. Another float check valve is provided in the form of a floating ball valve element 80 which precludes overflow of liquid from chamber 70 via inlet 75 and also prevents spilling if the apparatus 10 is inadvertantly tipped or inverted. That is, the ball valve element 80 is operable by gravity and by flotation to close off inlet port 74.

Figure 4:
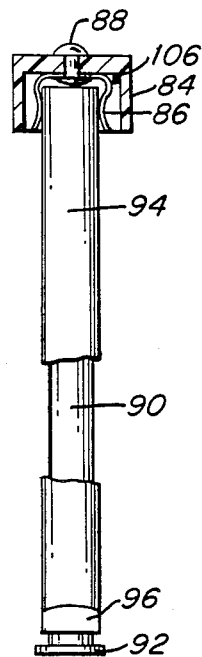
FIG. 4 is a partially sectioned and partially broken away detailed view of the cap assembly for the apparatus of the present invention.

Also as shown in FIGS. 3 and 4, tube element 20 provides an interior space 82 within wich a heat evolving means such as a solid agglomerate combustible fuel rod or chemical fuel element may be received. The heat evolved by such fuel that is transferred via the sidewalls of tube 20 to the liquid heat transfer medium 74 contained within chamber 72. The uppermost open end of tube 20 is closed by a cap member 84 which engages same in frictional engagement. Cap 84 preferably is of thermal insulating plastic such as the plastic composition characterized hereinabove. A fuel retaining structure is retained with respect to cap 84, being for example a spring clip structure 86 secured as by a rivet 88 centrally adjacent the innerside of cap 84. There may also be secured by rivet 88 a fuel stick supporting or aligning member 90 which projects downwardly of cap 84 so as to extend within tube 20 when cap 84 is installed thereon. A lower transverse end portion 92 of member 90 serves to form a floor under a fuel element 94 carried by the spring clips 86 to thereby capture ashes thereform and at least partially close off the lower open end 22 of tube 20 when in place. It is noted that the fuel element as shown may include an easy-igniting tip portion 96, for example a portion coated with safety match material, to facilitate easy ignition of the fuel element 94. This of course applies only to combustible type fuel elements.

It will be seen that with cap 84 in place and fuel element 94 secured with respect thereto the fuel element 94 will extend within tube 20 to permit evolution of heat therein for heating of the liquid medium 74. In the case of a combustible fuel element, ventilation to provide combustion oxygen is provided by vent slots 98 adjacent the lowermost end 22 of tube 20, and an adjustable vent port 100 adjacent the uppermost end thereof (FIG. 1).

Vent 100 comprises, as shown, an opening 102 formed adjacent the uppermost end of tube 20 for circumferentially overlapping relationship with a slot or cutout 104 formed in cap 84. by rotation of cap 84 to selected circumferential positions, the vent 100 may be set to fully open, partially open, or fully closed positions.

To facilitate setting of predetermined vent openings, cap 84 is provided with an interior key 106 (FIG. 4) which may be received in any of a plurality of key slots 108 formed at circumferentially spaced locations on the uppermost end of tube 20. The location of key slots 108 is determined, with respect to the location of opening 102, and correspondingly the location of key 106 is determined with respect to the location of slot 104 in cap 84 to provide a selection of several desirable settings for the degree of opening of vent 100. To attain any such degree of opening, cap 84 is lifted slightly, rotated to the desired position, and returned to its fully engaged position on tube 20 with key 106 engaged within the selected key slot 108.

In operation, as has been noted, chamber 72 is filled with a volume of liquid heat exchange medium 74 by injection thereof through port 75 and into chamber 70. The liquid thence flows via valve 76 into chamber 72 until chamber 72 is filled. The upper surface of the liquid volume may float valve seat 78 to close the valve 76.

Heat evolved from combustion or other exothermic reaction within tube 20 heats the fluid 74 in chamber 72 on a continuous basis. Application of manual pressure to resiliently flexible body member 14 closes valve 76 and causes the fluid 74 to flow via conduit 26 as indicated by arrows B to innersole 30. The conduit 26, the network of fluid flow passages in innersole 30, and conduit 28 preferably are filled solid with the liquid heat transfer medium 74. The above-described squeezing of body member 14 moves the fluid through conduit 26, the flow channels in innersole 30, and thence via the conduit 28 back to chamber 70 as indicated by arrows A. With each such squeeze, a given volume of heated fluid thus is moved toward and into the innersole 30, and an equal volume of fluid is deposited in chamber 70. The opening 75 maintains chamber 70 at ambient pressure and provides a vent for air therein to permit the fluid flow thereinto from conduit 28; however, if the fluid volume within chamber 70 approaches maximum capacity of the chamber, the float valve 80 closes inlet port 75 to preclude emission of fluid therefrom. As long as the squeezing of member 14 continues, valve 76 is also closed. Thus, the volume of chamber 70 defines the maximum volume of fluid which may be transferred with a single squeezing action.

Upon release of the squeezing action, member 14 resiles to its undeformed configuration due to the resiliency of material from which it is made, this permits valve 76 to gravitationally drop open whereby the fluid 74 within chamber 70 gravitationally returns to chamber 72 for reheating and subsequent recirculation thereof.

By repeated squeezing and release of body portion 14 as above described, repeated surges of heated fluid may be transferred to the innersole 30 or other article of wearing apparel to provide continuous warmth for the wearer. In addition to this function, because the heater 10 is carried at a convenient location for manual squeezing such as on the belt of a wearer, it is also conveniently located for use as a hand warmer.

Of course in the embodiment illustrated, one heater 10 is required for each of a pair of innersoles 30 in a pair of boots; however, it is contemplated that a single heater 10 may serve separate articles of apparel through provision of suitable junctions in the tubing network connecting same together.

According to the description hereinabove there is provided by the instant invention a novel and improved portable heater structure for convenient and reliable use in providing heated articles of wearing apparel. The structure of the invention provides for improved reliability of operation, structural integrity, simplicity of manufacture and assembly, and various other advantages as above described which offer a variety of corresponding benefits including low cost manufacture, sturdy structure, easy and convenient use, and greatly enhanced durability.

Of course, I have envisioned and anticipated various alternative and modified embodiments of the invention other than the above-described preferred embodiment, and such certainly would also occur to those versed in the art once apprised of my invention. It is therefore my intent that the invention be construed broadly and limited only by the scope of the claims appended hereto.

I claim:

1. In a portable heater for heating an article of wearing apparel or the like and comprising a compact closed container which defines a heating chamber for containing a liquid heat transfer medium therein and a second container received in the closed container in heat exchange relationship with the liquid heat transfer medium contained in the heating chamber, the second container being adapted to receive a heat evolving means therein, and conduit means communicating between the closed container and such an article of wearing apparel to define a flow circuit within which the contained heat transfer medium can circulate from the closed container to the article wearing apparel and back again thereinto the improvement comprising:

said heating chamber comprising a variable volume chamber having resiliently deformable portions which are deformable to provide a pumping action that imparts a flow impetus to said heat transfer medium within said heating chamber to induce circulation thereof within such flow circuit.

2. The improvement as claimed in claim 1 additionally including an ambient pressure return chamber cooperable with said conduit means to receive return flow of said heat transfer medium from such an article of wearing apparel.

3. The improvement as claimed in claim 2 additionally including return port means for conducting said heat transfer medium from said return chamber to said variable volume chamber.

4. The improvement as claimed in claim 3 wherein said return port means is operative to gravitationally conduct said heat transfer medium from said return chamber to said variable volume chamber.

5. The improvement as claimed in claim 4 wherein said return port means includes first one way flow check valve means to preclude reverse flow of said heat transfer medium from said variable volume chamber to said return chamber.

6. The improvement as claimed in claim 5 additionally including inlet port means associated with said return chamber for directing a quantity of heat transfer medium into said heating chamber.

7. The improvement as claimed in claim 6 wherein said return chamber forms a portion of said heating chamber.

8. The improvement as claimed in claim 7 wherein said inlet port means includes second one-way flow check valve means to preclude reverse flow of heat transfer medium therethrough from said return chamber.

9. The improvement as claimed in claim 8 wherein said first and second one-way flow check valve means are operable by flow impetus and gravity to preclude such reverse flow.

10. A portable heater for heating an article of wearing apparel comprising:

a compact container which defines a heating chamber for containing a quantity of liquid heat transfer medium therein;

a heating container received in said compact container and having exterior surface portions thereof located in heat exchange relationship with the interior of said heating chamber;

said heating container being adapted to receive therein a heat evolving means to provide thermal energy transfer via said exterior surface portions to such heat transfer medium within said heating chamber;

a fluid flow circuit comprised of a pair of conduits, one said conduit for conveying such heat transfer medium from said heating chamber to such an article of wearing apparel for heating thereof and the other said conduit for conveying such heat transfer medium from such an article of wearing apparel back to said heating chamber;

said heating chamber including a resiliently deformable variable volume portion associated with said one conduit and having a maximum volume, and being deformable under manual impetus to assume a reduced volume and to spontaneously return to said maximum volume upon cessation of such manual impetus; and valve means cooperable with said variable volume portion of said heating chamber to provide a positive displacement pump means for impelling a flow of such heat transfer medium via said one conduit though said fluid flow circuit in response to reduction of the volume of said variable volume portion.

11. The portable heater as claimed in claim 10 wherein said heating chamber additionally includes a return chamber portion maintained in fluid flow conducting relationship with said variable volume portion by flow port means communication therebetween to receive return heat transfer medium flow from such an article of wearing apparel via said other conduit and to intermittently direct the returned heat transfer medium into said variable volume portion.

12. The heater as claimed in claim 11 wherein said variable volume portion includes resilient perimeter wall portions which are manually deformable to provide reduction of the volume of said variable volume portion.

13. The heater as claimed in claim 12 additionally including vent means for maintaining said return chamber portion substantially continuously at ambient pressure for a predeterminable magnitude of such volume reduction during operation of said pump means.

14. The heater as claimed in claim 13 additionally including one-way flow check valve means associated with said flow port means for permitting fluid flow therethrough only from said return chamber portion to said variable volume chamber portion.

15. The heater as claimed in claim 14 wherein said return chamber portion, said variable volume chamber portion and said flow port means are arranged to provide gravitational flow of such returned heat transfer medium from said return chamber portion to said variable volume chamber portion.

16. A portable heater for providing heat to the person of a user comprising:

a first resiliently deformable body member having defined therein a variable volume portion of a fluid heating chamber;

a second body member disposed generally above and adjacent to said resiliently deformable body member and having defined therein a constant volume portion of said fluid heating chamber;

one-way flow port means communicating between said variable volume and constant volume heating chamber portions to permit fluid flow only from said constant volume portion to said variable volume portion;

a fluid flow circuit means for directing flow of fluid from said variable volume portion via said circuit means to said constant volume portion;

said variable volume portion being manually operable to reduce the volume thereof to impel such flow of fluid through said circuit means; and a heating container received at least partially within said constant volume and variable volume portions with peripheral portions thereof in heat exchange relationship with the interior of said constant and variable volume portions, and with at least an access portion thereof being disposed for access thereinto from the exterior of said first and second body members to accommodate placement of a heat evolving means within said heating container.

17. The portable heater as claimed in claim 16 wherein said access portion includes a removable cap means which is frictionally engageable on an access opening of said heating container.

18. The portable heater as claimed in claim 17 wherein said cap means includes vent aperture means which is registerable in a plurality of relative rotary positions with an associated vent aperture means formed in said access portion of said heating container whereby the degree of venting of the interior of said heating container to the ambient atmosphere is selectively controllable by adjustment of said cap means to selected rotary positions with respect to said access portion.

19. The portable heater as claimed in claim 18 wherein said heating container comprises an elongated generally tubular container passing entirely through said first and second body members such that opposite end portions of said heating container projects therefrom in opposite directions.

20. The portable heater as claimed in claim 19 additionally including clamp means disposed at longitudinally spaced locations on said tubular heating container for clamping said first and second body members in mutually adjacent relationship.

* * * * *